United States Patent

Yamane

[11] Patent Number: 6,015,434
[45] Date of Patent: Jan. 18, 2000

[54] ARTIFICIAL HEART PUMP

[75] Inventor: Takashi Yamane, Tsukuba, Japan

[73] Assignee: Agency of Industrial Science & Technology, Ministry of International Trade & Industry, Tokyo, Japan

[21] Appl. No.: 08/899,337

[22] Filed: Jul. 23, 1997

[30] Foreign Application Priority Data

Jul. 26, 1996 [JP] Japan .................................. 8-215242

[51] Int. Cl.$^7$ ...................................... A61M 1/10
[52] U.S. Cl. .................. 623/3; 417/420; 415/900
[58] Field of Search ................... 623/3; 600/16, 600/17; 415/900; 601/153; 417/420, 423.2

[56] References Cited

U.S. PATENT DOCUMENTS

| | | | |
|---|---|---|---|
| 5,195,877 | 3/1993 | Kletschka | 417/356 |
| 5,470,208 | 11/1995 | Kletschka | 415/900 X |
| 5,575,630 | 11/1996 | Nakazawa et al. | 417/420 |

FOREIGN PATENT DOCUMENTS

| | | | |
|---|---|---|---|
| 0 378 251 A3 | 7/1990 | European Pat. Off. | 417/420 |
| 1 165 144 | 3/1964 | Germany | 417/420 |
| 41 02 707 A1 | 8/1991 | Germany | 417/420 |
| 41 23 433 A1 | 2/1992 | Germany | 417/420 |
| 62-41992 | 2/1987 | Japan | 417/420 |

*Primary Examiner*—David H. Willse
*Attorney, Agent, or Firm*—Oblon, Spivak, McClelland, Maier & Neustadt, P.C.

[57] ABSTRACT

An artificial heart pump includes a casing having a pump chamber inside the casing and a partition that closes, in a fluid-tight manner, the bottom portion of the pump chamber, an impeller disposed inside the pump chamber so that it is rotatable about the axis of rotation and including an impeller shaft portion having a shaft hollow part and an impeller portion having an impeller hollow part extending radially and communicating with the shaft hollow part, the shaft hollow part and the impeller hollow part constituting a blood flow channel, a magnetic supporter for rotatably supporting the impeller within the casing in a direction normal to the axis of rotation, a pivot bearing for rotatably supporting the impeller within the casing in a direction of the axis of rotation, a rotating device accommodated within the casing below the pump chamber for rotating the impeller, and a magnetic coupler for transmitting the rotating force of the rotating device to the impeller.

2 Claims, 4 Drawing Sheets

ARTIFICIAL HEART PUMP

BACKGROUND OF THE INVENTION

1. Field of the Invention

The present invention relates to a centrifugal artificial heart pump and particularly to an improvement in a centrifugal artificial heart pump whose rotor is suspended in a noncontacting state by magnetic force.

2. Description of the Prior Art

It is impermissible for an artificial heart pump to promote blood coagulation (thrombogenesis) or blood cell destruction (hemolysis). In order to prevent blood coagulation (thrombogenesis), it is desirable that an artificial heart pump be configured to reduce the number of structural components hindering the blood from flowing through a blood flow channel within the artificial heart pump, enable the blood flow channel to have a large diameter, operate stably and reduce the displacement of movable structural components. In order to prevent blood cell destruction (hemolysis), it is desirable that an artificial heart pump be configured to shorten the length of the blood flow channel and lower the rotation speed of the movable structural components.

Artificial heart pumps can be classified into the diaphragm type, the tube type, the roller pressure type and the radial flow type that operates by rotational motion. Typical of the radial flow type is the centrifugal type.

Artificial heart pumps of the centrifugal type are generally equipped with a casing, a blood flow channel formed in the casing for introducing and guiding the flow of blood, an impeller rotatably disposed inside the casing for imparting centrifugal force to the blood flowing through the blood flow channel, and a motor for rotating the impeller.

There is proposed a centrifugal artificial heart pump 101 shown in FIG. 5. It comprises a casing 102 and an impeller 103 inside the casing 102. The impeller 103 is hollow and its hollow portion constitutes a blood flow channel 122. A shaft portion 114 of the impeller 103 is rotatably supported, with its periphery in a noncontacting state relative to the casing 102, by two sets of magnetic supporting devices 104 comprising inside supporting magnets 123 and outside supporting magnets 124, and the bottom of an impeller portion 115 of the impeller 103 is supported on the casing 102 by a pivot 125.

With the conventional artificial heart pump 101, however, since the length of the impeller shaft portion in the direction of a rotation axis is large, meaning that the blood flow channel 122 is long, blood cell destruction is apt to occur. Moreover, since the conventional artificial heart pump 101 is configured on the supposition that a drive motor is disposed at a middle position between the two magnets, it is difficult to obtain stable rotation.

Another conventional artificial heart pump was proposed in Artificial Viscera 24 (2) pp. 323–326 (1995), in which a blood flow channel is defined between the outer periphery of a rod-shaped impeller shaft portion and the inner periphery of a casing. In this structure, however, there is a possibility that outside supporting magnets have to be located within the blood flow channel from a standpoint of design. This will cause blood flow stagnation, resulting in that undesirable blood coagulation is likely to occur.

In view of the foregoing disadvantages, the present invention has been established and has as its object to provide an artificial heart pump that is configured to remove any structural component hindering the blood from flowing in through a blood flow channel within the artificial heart pump, enable the blood flow channel to have a large diameter, operate stably and have a simple structure, and can be miniaturized.

SUMMARY OF THE INVENTION

To attain the object, according to the present invention there is provided an artificial heart pump comprising a casing having a blood inlet, a blood outlet, a pump chamber inside the casing for communicating with the inlet and outlet, and a partition that closes, in a fluid-tight manner a bottom portion of the pump chamber; an impeller disposed inside the pump chamber so that it is rotatable about an axis of rotation and including an impeller shaft portion having a shaft hollow part and an impeller portion having an impeller hollow part extending radially and communicating with the shaft hollow part, the shaft hollow part and the impeller hollow part constituting a blood flow channel; a magnetic supporter including an inside supporting magnet attached to an outer periphery of the impeller shaft portion and an outside supporting magnet attached to an inner periphery of the casing for rotatably supporting the impeller within the casing in a direction normal to the axis of rotation; a pivot bearing including a pivot provided at a bottom surface of the impeller portion through which the rotation axis passes and a pivot receptacle formed on the partition of the casing for rotatably supporting the impeller within the casing in a direction of the axis of rotation; rotating means accommodated within the casing below the pump chamber for rotating the impeller; and a magnetic coupler including a set of first coupling magnets attached to the bottom surface of the impeller portion and a set of second coupling magnets opposed to the first coupling magnets across the partition for transmitting rotating force of the rotating means to the impeller.

In the artificial heart pump according to the present invention, since the impeller is hollow and its hollow part constitutes a blood flow channel, the blood flow channel is simple in shape and large in lateral cross section, and enables the blood to flow smoothly. Furthermore, since no structural component hindering the flow of blood, such as a magnet, exists in the blood flow channel, it is possible to suppress blood flow stagnation and blood coagulation from occurring.

The above and other objects, characteristic features and advantages of this invention will become apparent from the description made herein below with reference to the accompanying drawings.

DESCRIPTION OF THE PREFERRED EMBODIMENT

Figure 1A:
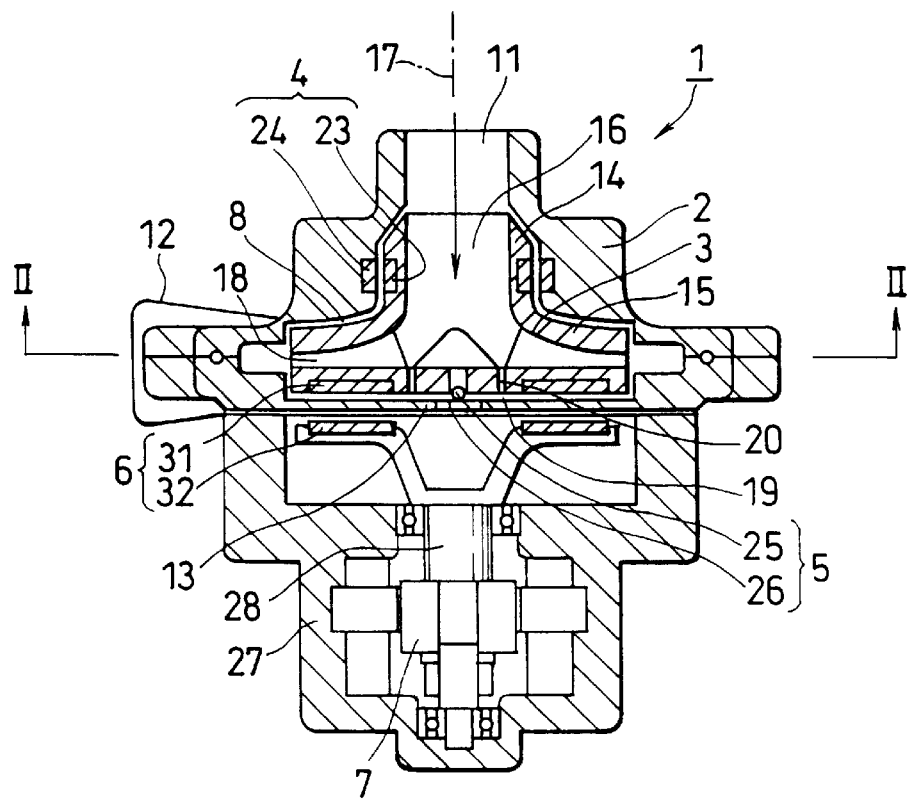
FIG. 1(a) is a longitudinal cross section illustrating an artificial heart pump that is an embodiment of the present invention.
Figure 2:
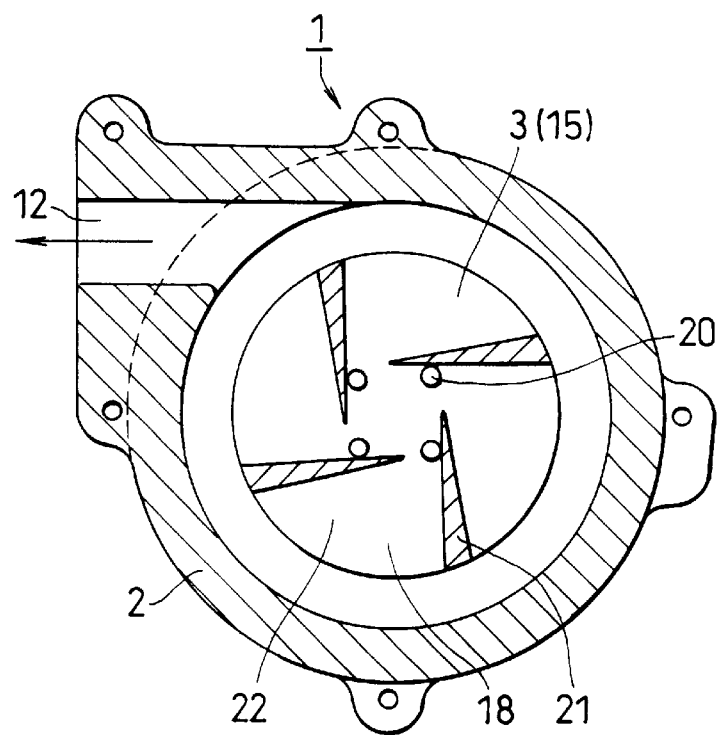
FIG. 2 is a cross section taken along line II—II in FIG. 1.

An embodiment of the present invention will be explained with reference to FIGS. 1 and 2. Reference numeral 1 denotes an artificial heart pump comprising a casing 2, an impeller 3, a magnetic supporter 4, a pivot bearing 5, a magnetic coupler 6 and a motor 7, provided that the motor 7 includes a conventional motor having a movable portion and a set of coils without a movable portion which will be described later.

The casing 2 has a blood inlet 11, a blood outlet 12, a pump chamber 8 communicating with the inlet and outlet 11 and 12, and a partition 13 that closes, in a fluid-tight manner, the bottom portion of the pump chamber 8.

The impeller 3 includes an impeller shaft portion 14 and an impeller portion 15 integral with the impeller shaft portion 14 and is disposed within the pump chamber 8.

The impeller shaft portion 14 is formed therein with a shaft hollow part 16 extending along the axis of rotation and constituting a blood flow channel. The impeller portion 15 is formed therein with an impeller hollow part 18 extending from the axis of rotation to the periphery of the impeller. The impeller hollow part 18 is partitioned by vanes 21 into a plurality of radial blood-flow channel segments 22. The impeller portion 15 is formed with washout through-holes 20 communicating the impeller hollow part 18 and a gap 19 between the bottom surface of the impeller portion 15 and the partition 13. The magnetic supporter 4 comprises an inside supporting magnet 23 mounted on the outer periphery of the impeller 3 and an outside supporting magnet 24 mounted on the inner periphery of the casing 2 for rotatably supporting the impeller 3 in the direction normal to the axis of rotation 17. Since the inside and outside magnets 23 and 24 are formed of repelling magnets, the impeller 3 is rotatably supported in a noncontacting state relative to the casing 2.

The pivot bearing 5 comprises a pivot 25 provided at the bottom surface of the impeller portion 15 through which the rotation axis 17 passes and a pivot receptacle 26 formed on the partition 13. On the other hand, the casing 2 has at its lower portion a motor chamber 27 to which the motor 7 is mounted.

Figure 1B:
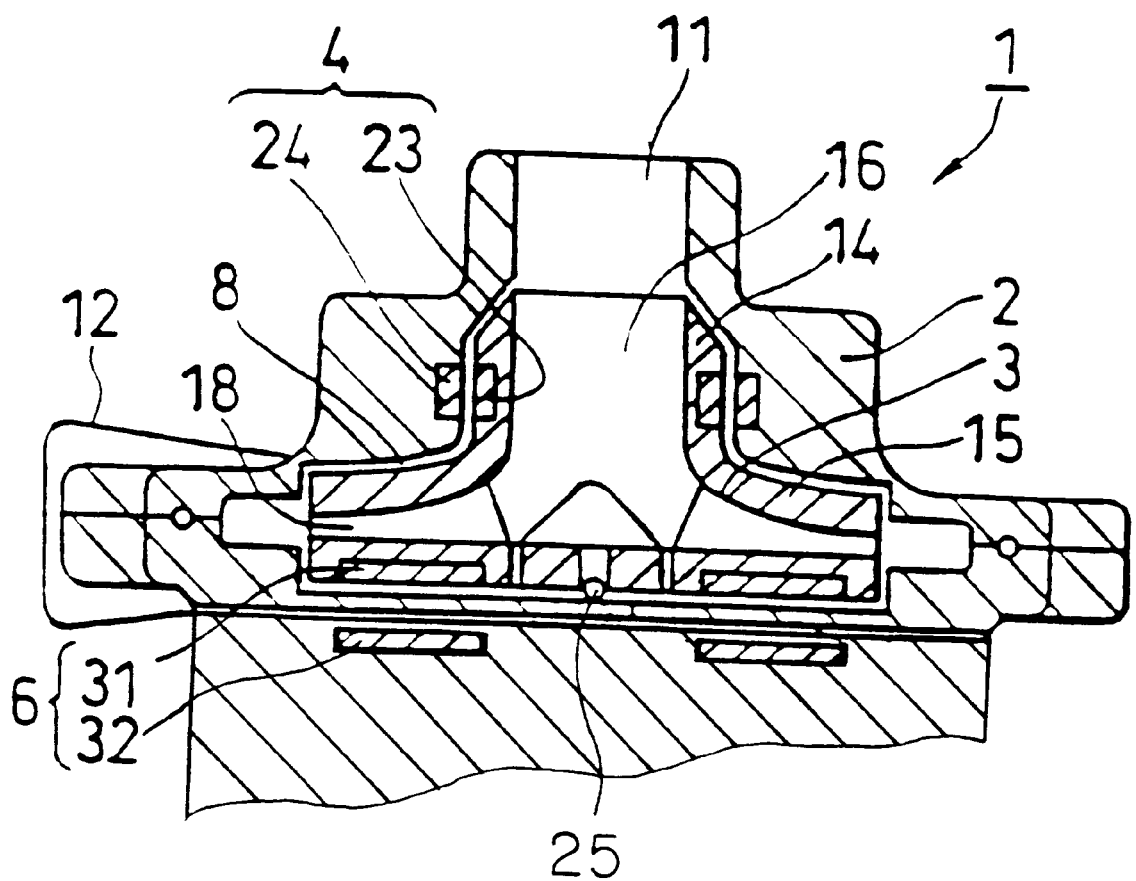
FIG. 1(b) is a longitudinal cross section illustrating a modification of FIG. 1(a); which uses a set of coils.
Figure 3:
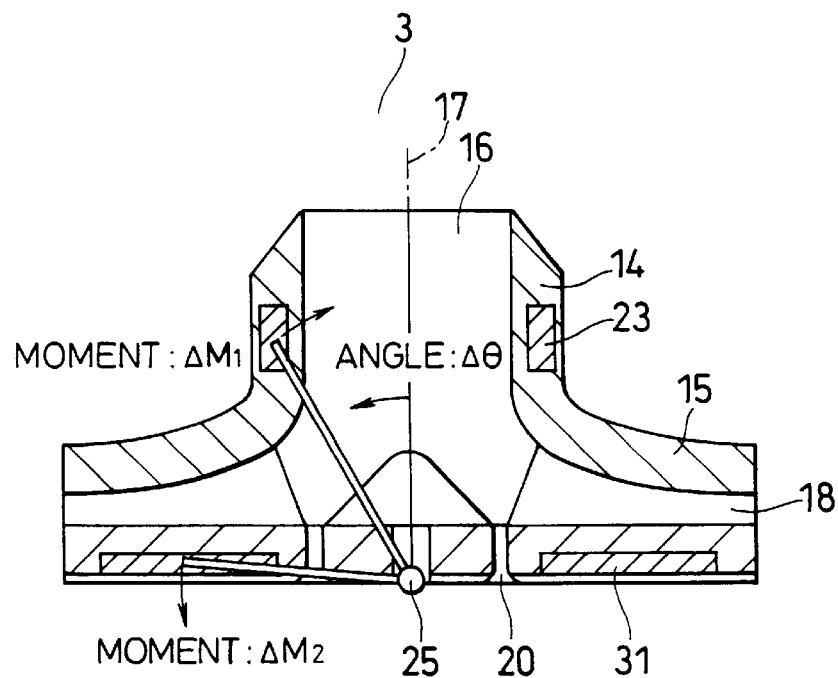
FIG. 3 is a longitudinal cross section illustrating an impeller of the artificial heart pump shown in FIG. 1.

The rotation of an output shaft 28 of the motor 7 is transmitted to the impeller 3 by the magnetic coupler 6 which includes a first coupling magnet 31 mounted on the bottom surface of the impeller 3 and a second coupling magnet 32 opposed to the first coupling magnet 31 across the partition 13 attached to the top of the output shaft 28 of the motor 7. It should be noted, however, that a combination of the motor 7, motor output shaft 28 and coupling magnets can be replaced with a set of coils that can produce the same rotating magnetic field as permanent magnets by switching an electric current. That is to say, as shown in FIG. 1(b), instead of the second coupling magnet 32, a coil 32' can be used which is wound around the stator and disposed so as to face the first coupling magnetic 31 thereby inducing a rotating magnetic field for rotating the impeller 3. Design conditions of the inside and outside supporting magnets 23 and 24 constituting the magnetic supporter 4 and the sets of first and second coupling magnets 31 and 32 constituting the magnetic coupler 6 are determined by $(\Delta M_1 + \Delta M_2)/\Delta\Theta < 0$ and $M_c > PQ/\omega$, wherein $\Delta M_1$ stands for a moment by the magnetic supporter 4, $\Delta M_2$ for a moment by the magnetic coupler 6 and $\Delta\theta$ for an angle of inclination of the impeller shaft portion as shown in FIG. 3, and $M_c$ stands for a decoupling torque, $\omega$ for the number of revolutions, P for the blood flow pressure, and Q for the flow rate of the blood.

The operation of the artificial heart pump 1 thus configured will be described.

Magnetic repulsion arises between the N and S poles of the inside supporting magnet 23 of the magnetic supporter 4 and the N and S poles of the outside supporting magnet 24 thereof. As a result, the impeller is rotatably supported in the direction normal to the axis of rotation 17 in a noncontacting state relative to the casing 2. With the impeller 3 supported in non-contact with the housing 2, the impeller 3 is driven by the motor 7. The rotation of the output shaft 28 of the motor 7 is transmitted from the set of second coupling magnets 32 of the magnetic coupler 6 to the set of first coupling magnets 31 thereof. The magnetic flux of the set of second coupling magnets 32 passes through the partition 13 and reaches the set of first coupling magnets 31, thereby allowing the set of second coupling magnets 32 to attract the set of first coupling magnets 31 into a coupled state. When the impeller is rotated, the blood is sucked in from the blood inlet 11 of the casing 2. The blood thus sucked in flows through the shaft hollow part 16 of the impeller shaft portion 14 into the impeller portion 15, in which the blood is centrifuged and guided by the vanes 21 to radially flow through the plurality of blood flow channel segments 22 and is then sent out from the blood outlet 12.

Figure 4:
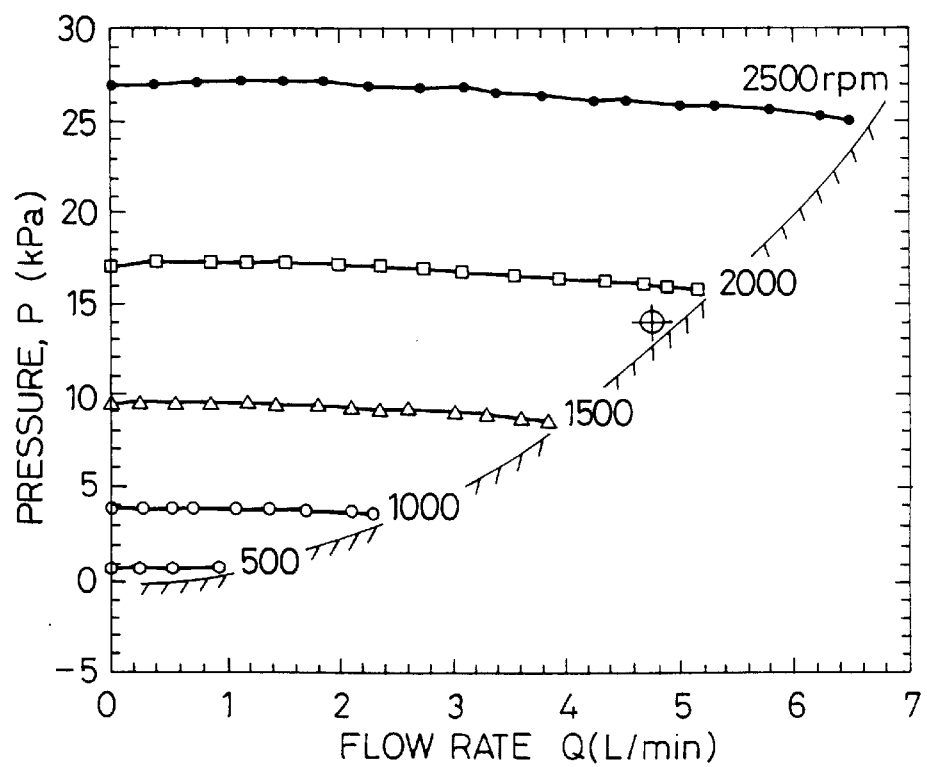
FIG. 4 is a graph showing the relationship between the pressure generated by the flow of blood and the flow rate of the blood in the artificial heart pump according to the present invention.
Figure 5:
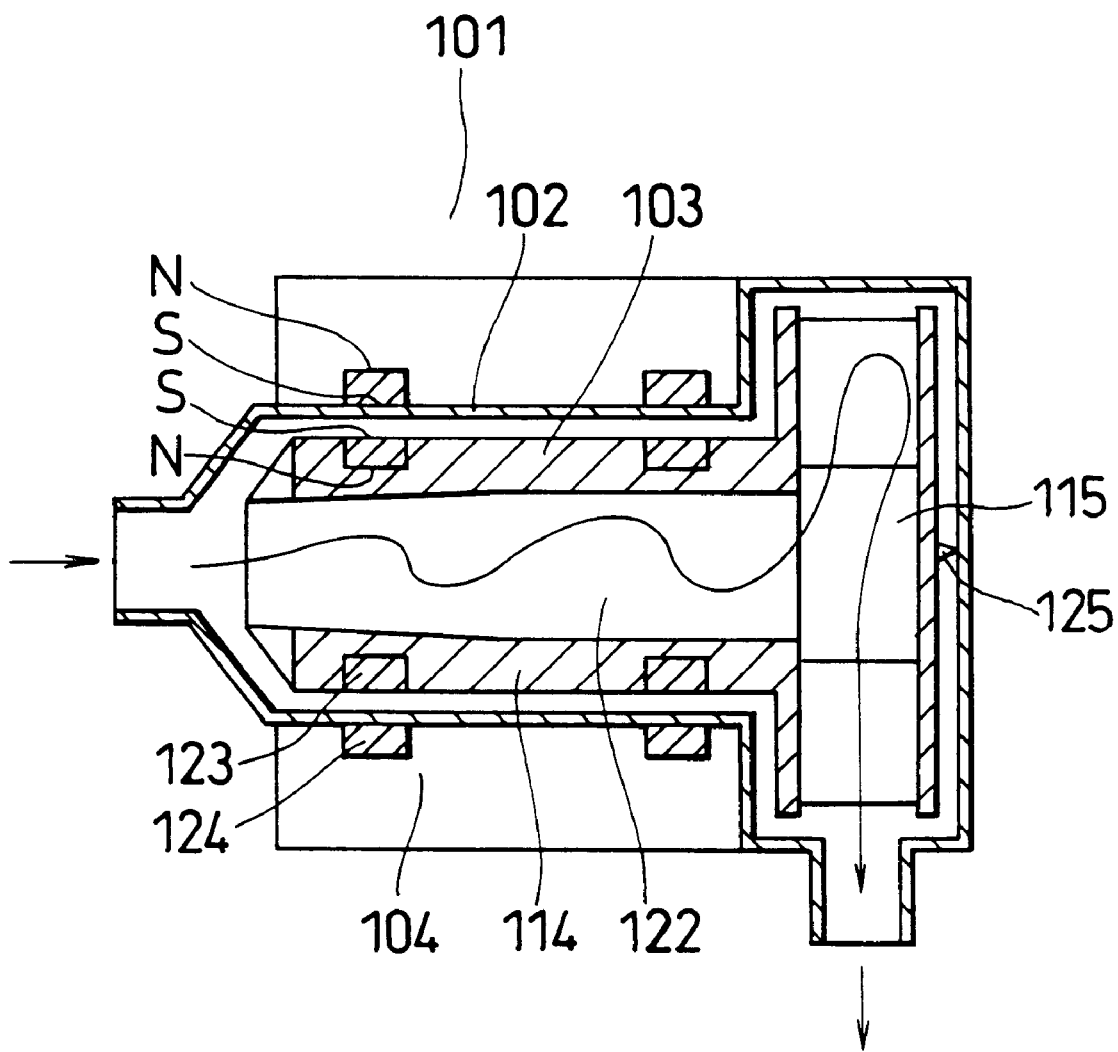
FIG. 5 a longitudinal cross section for explaining a conventional artificial heart pump.

A sample of an artificial heart pump of the present invention was prepared and an experiment was conducted at a temperature of 37° C. using 45% by weight of a glycerol solution as quasi-blood. As a result, a stable movement of the sample could be visually confirmed in the operation region shown in FIG. 4. In addition, it was confirmed that the quasi-blood could be sent out at a flow rate of 5 liters/min. under a pressure of 14 kPa (at a position marked by ⬧ in FIG. 4) required or an artificial heart.

In the artificial heart pump 1 of the present invention, since the impeller 3 is hollow and its hollow portion constitutes a blood flow channel, the blood flow channel is simple in shape and large in lateral cross section. In addition, there is no magnet or other structural components hindering the flow of blood in the blood flow channel. Therefore, the blood can flow smoothly in the blood flow channel.

The magnetic supporter 4 utilizes magnetic repulsion between the inside and outside supporting magnets 23 and 24, and the magnetic coupler 6 utilizes magnetic attraction between the sets of first and second coupling magnets 31 and 32. Since the two magnetic devices are separated from each other such that the magnetic supporter 4 is disposed at the impeller shaft portion 14 and the magnetic coupler 6 is disposed at the bottom of the impeller portion 15, the natural frequency of the impeller 3 can be kept high and the rotation of the impeller 3 can be kept stable. This can make a flow of blood smooth. In addition, since the magnetic coupler 6 is disposed at the bottom of the impeller 3, the length of the impeller shaft portion 14 of the impeller 3 can be shortened in the axis of rotation. This can miniaturize an artificial heart pump 1.

As has been described in the foregoing, according to the present invention there can be provided an artificial heart pump of a simple structure, in which no hindrance to a flow of blood exists in the blood flow channel and the blood flow channel is wide and short, and which can be operated stably and miniaturized.

What is claimed is:

1. An artificial heart pump comprising:
   a casing having a blood inlet, a blood outlet, a pump chamber inside the casing for communicating with the inlet and outlet, and a partition that closes, in a fluid-tight manner, a bottom portion of the pump chamber;
   an impeller disposed inside the pump chamber so that it is rotatable about an axis of rotation and including an impeller shaft portion having a shaft hollow part and an impeller portion having an impeller hollow part extending radially and communicating with the shaft hollow part, the shaft hollow part and the impeller hollow part constituting a blood flow channel;

a magnetic supporter including an inside supporting permanent magnet attached to an outer periphery of the impeller shaft portion and an outside supporting permanent magnet attached to an inner periphery of the casing so that the inside and outside supporting permanent magnets repel each other and the impeller is rotatable supported within the casing in a direction normal to the axis of rotation;

a pivot bearing including a pivot provided at a bottom surface of the impeller portion through which the rotation axis passes and a pivot receptacle formed on the partition of the casing for rotatably supporting the impeller within the casing in a direction of the axis of rotation;

rotating means accommodated within the casing below the pump chamber for rotating the impeller; and a magnetic coupler including a set of first coupling magnets attached to the bottom surface of the impeller portion and a set of second coupling magnets opposed to the set of first coupling magnets across the partition for transmitting rotating force of the rotating means to the impeller.

2. The artificial heart pump according to claim 1, wherein said rotating means is a set of coils that produce a rotating magnetic field.

* * * * *